(12) United States Patent
Mishima

(10) Patent No.: US 8,206,837 B2
(45) Date of Patent: *Jun. 26, 2012

(54) INTERVENTIONAL MEDICAL DEVICE

(75) Inventor: Katsuro Mishima, Yugawara-cho (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 676 days.

This patent is subject to a terminal disclaimer.

(21) Appl. No.: 11/862,245

(22) Filed: Sep. 27, 2007

(65) Prior Publication Data

US 2008/0171217 A1    Jul. 17, 2008

Related U.S. Application Data

(60) Provisional application No. 60/880,712, filed on Jan. 17, 2007.

(30) Foreign Application Priority Data

Jan. 12, 2007  (JP) ................................. 2007-005001
Jun. 27, 2007  (JP) ................................. 2007-169348

(51) Int. Cl.
*B32B 15/04* (2006.01)
*B32B 15/18* (2006.01)
*B32B 15/20* (2006.01)
*A61M 25/00* (2006.01)
*A61M 25/16* (2006.01)

(52) U.S. Cl. ........ 428/615; 428/586; 428/592; 428/649; 428/660; 428/680; 428/685; 600/585; 604/525

(58) Field of Classification Search .............. 428/586, 428/592, 666, 548, 615, 649, 660, 680, 681, 428/684, 685
See application file for complete search history.

(56) References Cited

U.S. PATENT DOCUMENTS

| | | | |
|---|---|---|---|
| 4,574,878 A * | 3/1986 | Sugiyama et al. | 165/134.1 |
| 4,925,445 A | 5/1990 | Sakamoto et al. | |
| 5,069,226 A | 12/1991 | Yamauchi et al. | |
| 5,238,004 A | 8/1993 | Sahatjian et al. | |
| 5,269,759 A | 12/1993 | Hernandez et al. | |

(Continued)

FOREIGN PATENT DOCUMENTS

JP   1-124473 A   5/1989

(Continued)

OTHER PUBLICATIONS

Machine Translation, Yamada, JP 2003-159333, Jun. 2003.*

(Continued)

*Primary Examiner* — Michael Lavilla
(74) *Attorney, Agent, or Firm* — Buchanan Ingersoll & Rooney PC

(57) ABSTRACT

According to one aspect, an interventional medical device includes a first wire disposed at a distal end and made of an alloy containing Ti and a transition metal other than Ti and Cr, and a second wire disposed at a proximal end of the first wire and made of an alloy containing Cr and a transition metal other than Cr and Ti. The device may include the first wire and the second wire being brazed to each other by a brazing material. The brazing material contains a metal whose ionization tendency is more basic than Ti and Cr. The brazing material is preferably an Ag—Mg alloy or an Ni—Mg alloy, and preferably has a composition near the eutectic point.

14 Claims, 10 Drawing Sheets

U.S. PATENT DOCUMENTS

| | | | |
|---|---|---|---|
| 5,354,623 A | 10/1994 | Hall | |
| 5,368,049 A | 11/1994 | Raman et al. | |
| 5,402,799 A | 4/1995 | Colon et al. | |
| 5,411,476 A | 5/1995 | Abrams et al. | |
| 5,452,726 A | 9/1995 | Burmeister et al. | |
| 5,497,786 A | 3/1996 | Urick | |
| 5,498,250 A | 3/1996 | Prather | |
| 5,512,081 A * | 4/1996 | DelGrosso et al. | 75/255 |
| 5,695,111 A | 12/1997 | Nanis et al. | |
| 5,772,609 A | 6/1998 | Nguyen et al. | |
| 5,797,857 A | 8/1998 | Obitsu | |
| 5,876,356 A | 3/1999 | Viera et al. | |
| 5,924,998 A | 7/1999 | Cornelius et al. | |
| 5,951,494 A | 9/1999 | Wang et al. | |
| 6,001,068 A | 12/1999 | Uchino et al. | |
| RE36,628 E | 3/2000 | Sagae et al. | |
| 6,093,157 A | 7/2000 | Chandrasekaran | |
| 6,165,292 A | 12/2000 | Abrams et al. | |
| 6,234,981 B1 | 5/2001 | Howland | |
| 6,390,992 B1 | 5/2002 | Morris et al. | |
| 6,520,923 B1 | 2/2003 | Jalisi | |
| 6,602,208 B2 | 8/2003 | Jafari | |
| 6,679,853 B1 | 1/2004 | Jalisi | |
| 6,702,762 B2 | 3/2004 | Jafari et al. | |
| 7,762,962 B2 * | 7/2010 | Mishima | 600/585 |
| 2002/0087099 A1 * | 7/2002 | Nanis et al. | 600/585 |
| 2004/0030266 A1 | 2/2004 | Murayama et al. | |
| 2004/0039308 A1 | 2/2004 | Murayama et al. | |
| 2004/0039309 A1 | 2/2004 | Murayama et al. | |
| 2004/0106878 A1 * | 6/2004 | Skujins et al. | 600/585 |
| 2005/0142377 A1 * | 6/2005 | Hall | 428/660 |
| 2005/0152731 A1 | 7/2005 | Mishima et al. | |
| 2006/0027625 A1 * | 2/2006 | Dockus et al. | 228/56.3 |
| 2008/0171852 A9 * | 7/2008 | Kim et al. | 530/328 |

FOREIGN PATENT DOCUMENTS

| | | | |
|---|---|---|---|
| JP | 2003-159333 | * | 6/2003 |

OTHER PUBLICATIONS

Cheng et al., "Predicting Tensile Properties of the Bulk 96.5Sn-3.5Ag Lead-free Solder," in J. Electronic Materials., 32 (6), 2003 (no. month), pp. 1-19, downloaded from www.boulder.nist.gov on Nov. 21, 2011.*

* cited by examiner

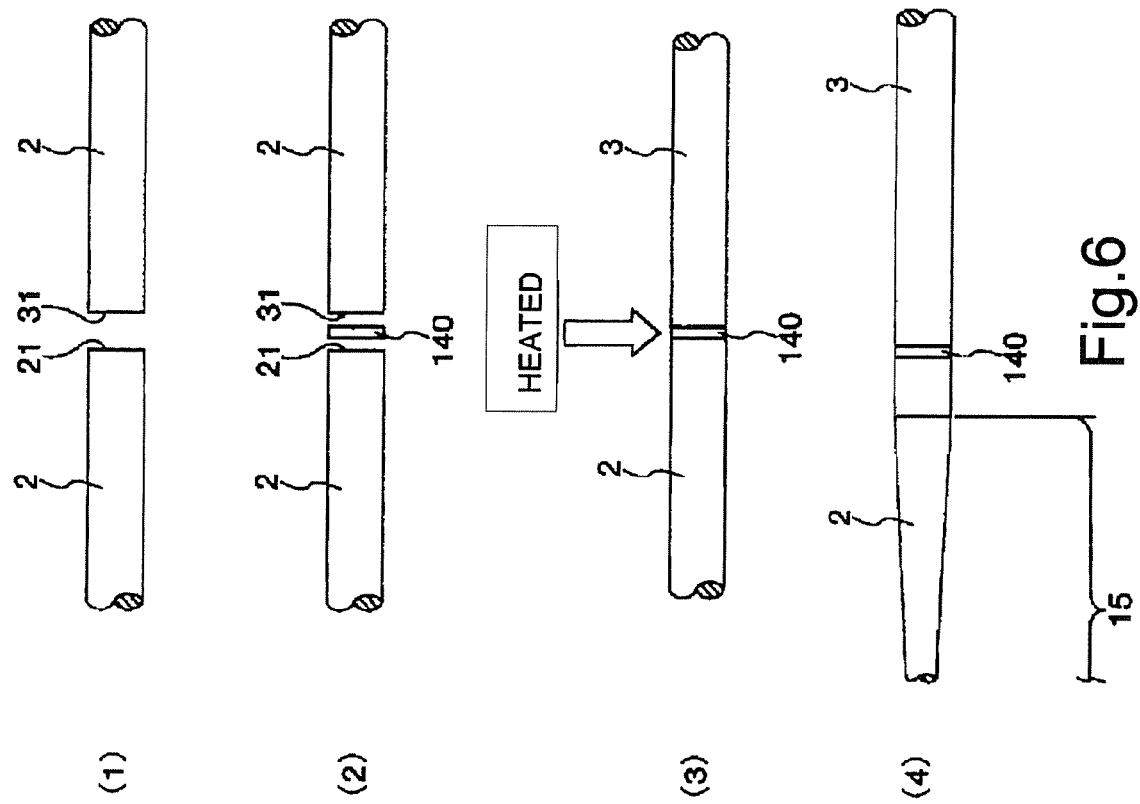

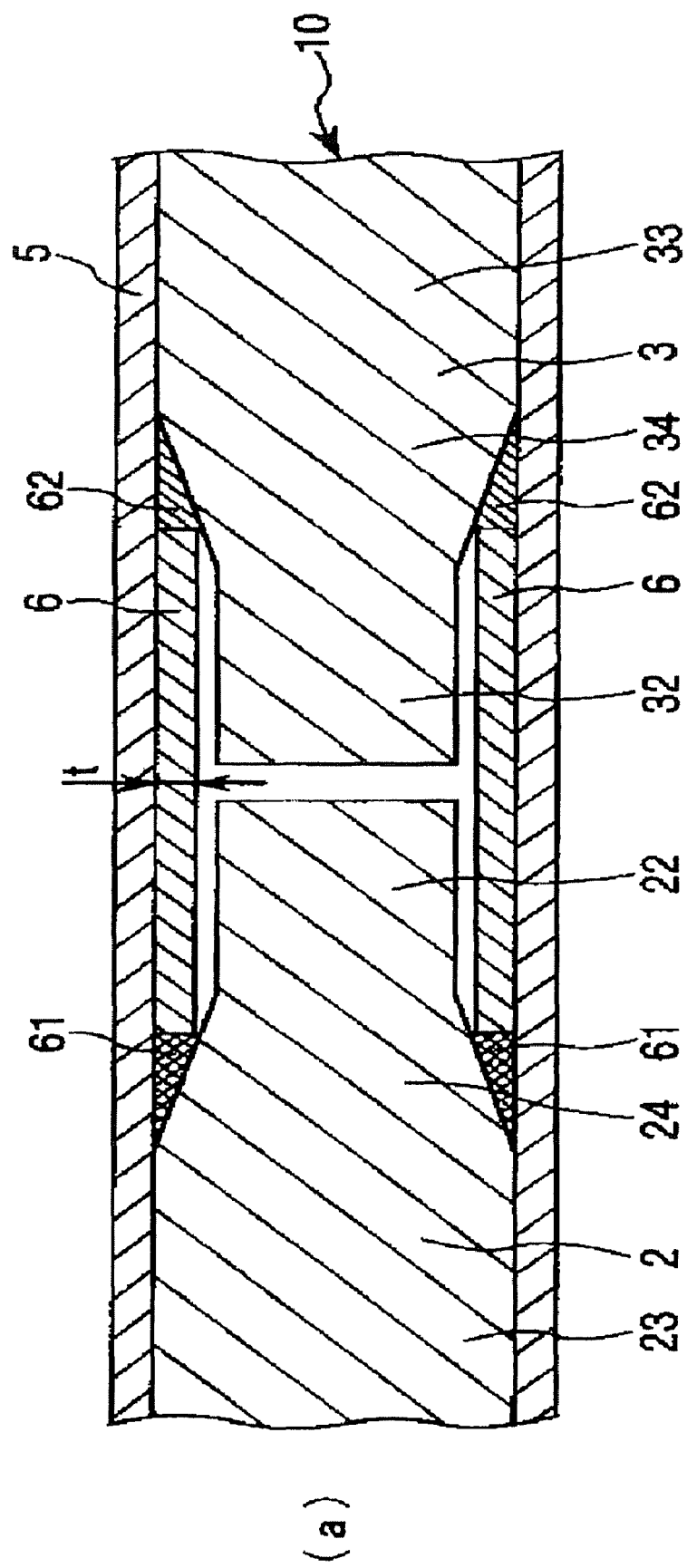

INTERVENTIONAL MEDICAL DEVICE

This application claims priority under 35 U.S.C. §119(e) with respect to U.S. provisional Application No. 60/880,712 filed on Jan. 17, 2007, and is also based on and claims priority under 35 U.S.C. §119(a) with respect to Japanese Application No. 2007-5001 filed on Jan. 12, 2007 and Japanese Application No. 2007-169384 filed on Jun. 27, 2007, the entire content of all of which is incorporated herein by reference.

TECHNOLOGICAL FIELD

The present invention generally pertains to a brazing material, an interventional medical device and a joined assembly. More specifically, the invention relates to a brazing material for use in brazing members to each other, a guide wire which employs such a brazing material and which is used to introduce a catheter into a body cavity such as a blood vessel, and a joined assembly employing such a brazing material.

BACKGROUND DISCUSSION

Guide wires are used to guide catheters for use in the treatment of body regions that are difficult to operate on surgically, such as PTCA (Percutaneous Transluminal Coronary Angioplasty), the treatment of body regions through minimally invasive surgery, and the inspection of blood vessels by cardiac angiography. For example, for performing PTCA using a guide wire, the distal end of the guide wire is positioned to project from the distal end of a balloon catheter, and the guide wire together with the balloon catheter is inserted into the blood vessel up to a position near the constricted area of the blood vessel in question for guiding the distal end of the balloon catheter to the position near the constricted area.

Blood vessels oftentimes possess a complexly curved shape. A guide wire used to insert a balloon catheter into a blood vessel is required to be pliable and recoverable when it is bent, to possess pushability and torque transmittability characteristics (collectively referred to as "operability") for transmitting an action or operation (force) on the proximal end of the guide wire to the distal end of the guide wire, and to exhibit kink resistance qualities (bend resistance), etc. Particularly for imparting pliability characteristics to the guide wire, it has been proposed to use a metal coil which is pliable when bent, disposed around a thin distal end core of the guide wire and a superelastic wire of Ni—Ti or the like used as the core of the guide wire to make the guide wire pliable and recoverable.

Known guide wires have a core made essentially of one type of material. In order to increase the operability of the guide wire, the core is made of a material having a relatively high modulus of elasticity. As a result, the distal end of the guide wire tends to be less pliable. If the core of the guide wire is made of a material having a relatively low modulus of elasticity in order to make the distal end of the guide wire sufficiently pliable, the operability of the guide wire at the proximal end is lost. A need exists for a guide wire which preferably meets the requirements for both pliability and operability.

In an attempt to address such need, there has been proposed in U.S. Pat. No. 6,001,068 a guide wire including a flexible first wire disposed on a distal end side and a highly rigid second wire disposed on a proximal end side, the first and second wires being joined to each other by brazing. This guide wire possesses increased pliability at the distal end and increased rigidity at the proximal end for better operability.

However, if the first wire and the second wire are covered with an oxide film, the brazing material fails to sufficiently wet the oxide film. As a consequence, it is hard to securely braze the first wire and the second wire to each other. Since Cr and Ti form a chemically stable oxide film, they are liable to produce the above tendency. Also, it is particularly difficult to firmly braze wires that are made of stainless steel or Ni—Ti-based alloy.

Attempts have been made to remove the oxide film by using a flux for reducing the oxide film. However, as the flux fails to sufficiently remove the oxide film, the bonding strength of the brazed joint formed using the flux is not large enough.

SUMMARY

A brazing material for brazing a first member made of an alloy containing Ti (titanium) and a transition metal other than Ti and Cr (chromium) and a second member made of an alloy containing Cr and a transition metal other than Cr and Ti. The brazing material contains a metal whose ionization tendency is more basic than Ti and Cr.

According to one aspect, the brazing material is preferably made of an eutectic alloy having an eutectic composition. The metal whose ionization tendency is preferably more basic than Ti and Cr includes Mg (magnesium). The content of Mg in the brazing material is preferably in the range from 10 to 96 atm %.

The brazing material is preferably made of an alloy of Mg and additionally Ag (silver), Ni (nickel), Au (gold), or Cu (copper). The brazing material can be made of an Ag—Mg alloy, with the content of Mg in the Ag—Mg alloy being in the range from 30 to 36 atm % or from 79 to 85 atm %. The brazing material can also be made of an Ni—Mg alloy, with the content of Mg in the Ni—Mg alloy being in the range from 17 to 23 atm % or from 86 to 92 atm %. The brazing material may also be made of an Au—Mg alloy, with the content of Mg in the Au—Mg alloy being in the range from 30 to 96 atm %. The brazing material can also be made of an Au—Mg alloy, with the content of Mg in the Au—Mg alloy in the range from 30 to 36 atm %, or from 61 to 72 atm %, or from 90 to 96 atm %. The brazing material can further be made of a Cu—Mg alloy, with the content of Mg in the Cu—Mg alloy in the range from 10 to 88 atm %. With the brazing material made of a Cu—Mg alloy, the content of Mg in the Cu—Mg alloy is in the range from 20 to 26 atm %, or from 55 to 61 atm %, or from 82 to 88 atm %.

The first member is preferably made of an Ni—Ti-based alloy and the second member is preferably made of stainless steel. One of the first member and the second member may include a first wire disposed at a distal end and the other of the first member and the second member includes a second member disposed at a proximal end of the first wire. One of the first member and the second member may include a wire body and the other of the first member and the second member includes a helical coil covering a distal end portion of the wire body. One of the first member and the second member may include one of two wires and the other of the first member and the second member includes a tubular body connecting the two wires to each other.

Another aspect involves an interventional device.

According to another aspect, an interventional medical device may include a first member and a second member which are brazed to each other by a brazing material comprising a metal whose ionization tendency is more basic than Ti and Cr, wherein the metal includes and the brazing material is made of an eutectic alloy having an eutectic composition.

The first member is preferably made of a Ni—Ti-based alloy and said second member is made of stainless steel.

Another aspect involves a joined assembly. The joined assembly may include a first member made of an alloy containing Ti (titanium) and a transition metal other than Ti and Cr (chromium), and a second member made of an alloy containing Cr and a transition metal other than Cr and Ti, with the first member and the second member being brazed to each other by a brazing material containing a metal whose ionization tendency is more basic than Ti and Cr.

BRIEF DESCRIPTION OF THE DRAWING FIGURES

The foregoing and additional features will become more apparent from the following detailed description considered with reference to the accompanying drawing figures in which like features are designated by like reference numerals.

Figure 5A:
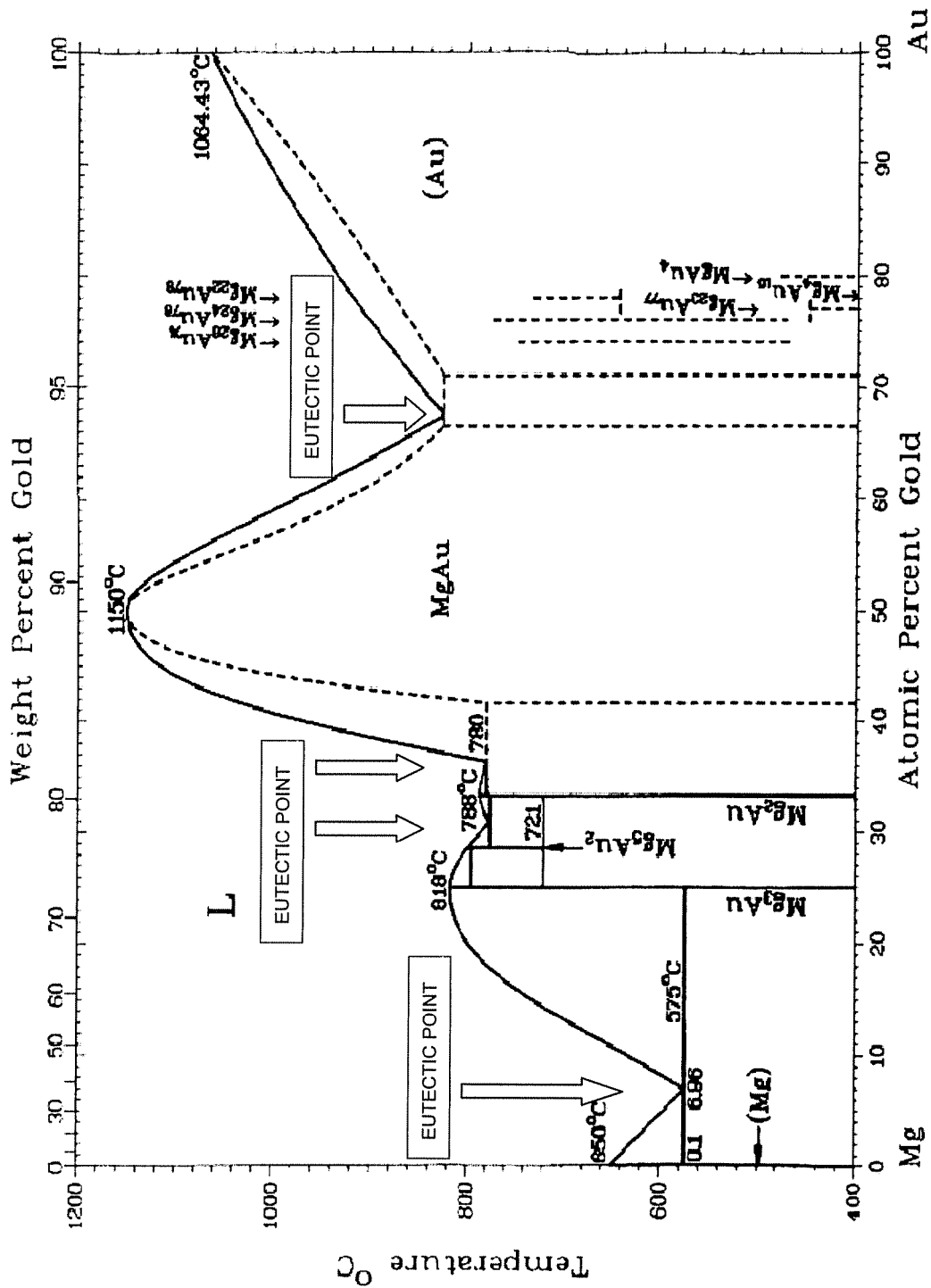
Figure 5B:
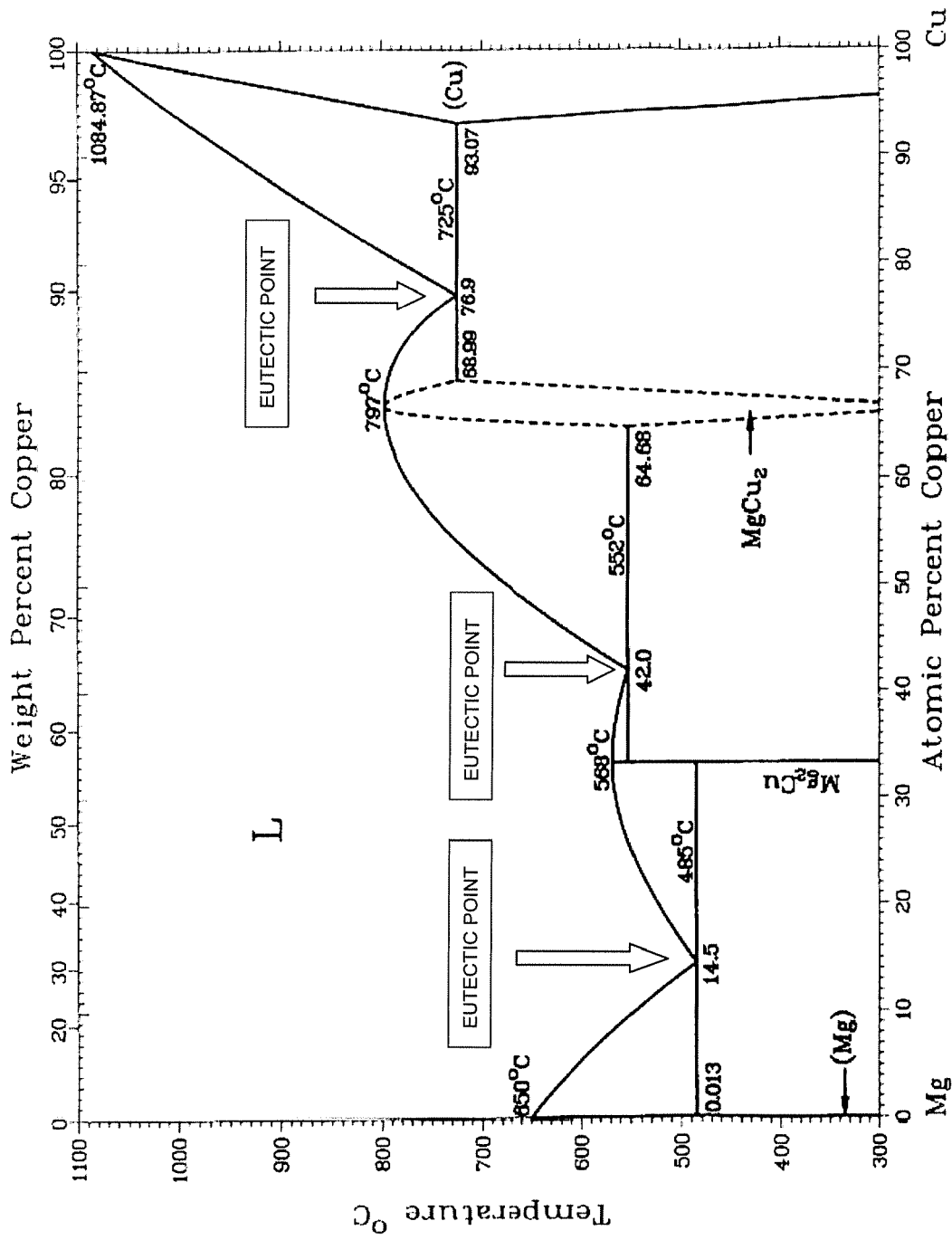

FIGS. 5(a) and 5(b) are phase diagrams of an Au—Mg alloy and a Cu—Mg alloy.

Figure 1:
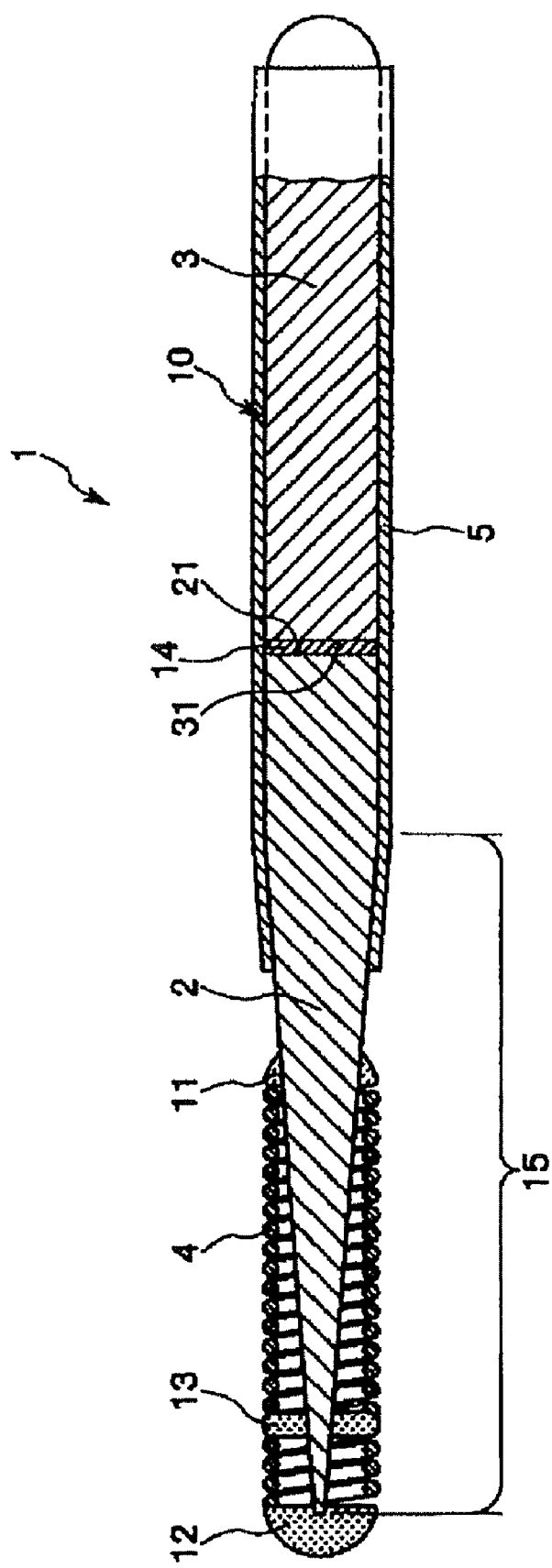
FIG. 1 is a longitudinal cross-sectional view of a guide wire forming an interventional medical device according to a first embodiment disclosed herein.

FIGS. 6(1) through 6(4) are schematic illustrations of a process of brazing a first wire and a second wire of the guide wire shown in FIG. 1.

Figure 7:
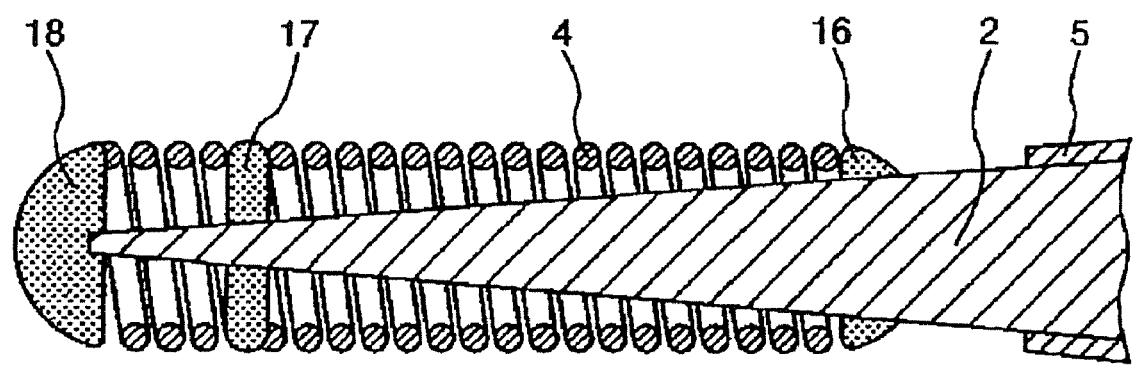

FIG. 7 is a longitudinal cross-sectional view of a portion of guide wire forming an interventional medical device according to a second embodiment.

FIG. 8(a) is a longitudinal cross-sectional view of a portion of a guide wire forming an interventional medical device according to a third embodiment.

Figure 8B:
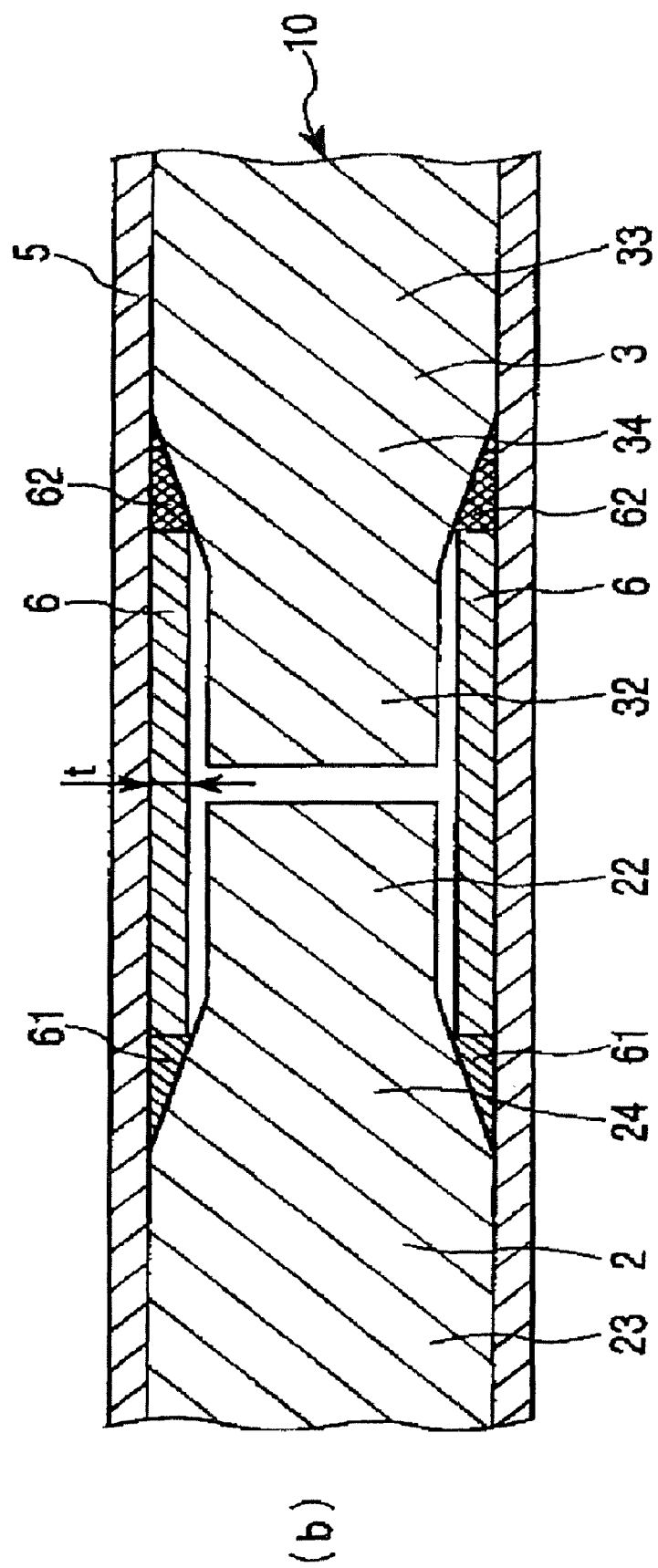

FIG. 8(b) is a longitudinal cross-sectional view of a portion of a guide wire forming an interventional medical device according to a fourth embodiment.

DETAILED DESCRIPTION

According to the disclosure here, a brazing material is used to braze a first member made of an alloy containing Ti (titanium) and a transition metal other than Ti and Cr (chromium) and a second member made of an alloy containing Cr and a transition metal other than Cr and Ti, wherein the brazing material contains a metal whose ionization tendency is more basic than Ti and Cr.

The first member and the second member that are brazed by the brazing material disclosed here may be any members. According to a first embodiment of the present invention, a first wire disposed on a distal end side and a second wire disposed on a proximal end side will be described as an example of the first member and the second member, respectively. More specifically, the description below describes an interventional medical device in the form of a guide wire produced by brazing a first wire and a second wire to each other.

For reference purposes, the right side in FIGS. 1, 2, 7, 8(a) and 8(b) are referred to as the "proximal end" and the left side is referred to as the "distal end". To help facilitate a better understanding, the interventional medical device (e.g., guide wire) is shown in FIGS. 1, 2, 7, 8(a) and 8(b) at a reduced scale in the longitudinal direction and at an exaggerated scale in the transverse direction. Thus, the illustrated ratio between longitudinal and transverse dimensions differs from the actual ratio.

A guide wire 1 shown in FIG. 1, constituting one embodiment of an interventional medical device, is a catheter guide wire for insertion into a catheter. The guide wire 1 includes a wire body 10 comprised of a first member or first wire 2 disposed on a distal end portion of the guide wire and a second member or second wire 3 disposed on a proximal end portion of the guide wire, and a helical coil 4 disposed on or around at least a portion of the first wire 2. The second wire 3 is joined to the first wire 2.

The entire length of the guide wire 1 is not limited to any specific value, but should preferably be in the range from about 200 to 5000 mm. The outside diameter of the wire body 10 (i.e., the outside diameter of the constant-outside-diameter portion of the wire body 10 as illustrated in FIG. 1) is also not limited to any particular value, though should preferably be in the range from about 0.2 to 1.2 mm.

The first wire 2 is made of a wire material which is elastic. The length of the first wire 2, though not limited to a specific length, is preferably in the range from about 20 to 1000 mm.

In the illustrated embodiment, the outside diameter of the first wire 2 is substantially constant over a certain length from the proximal end, followed by a portion of progressively smaller outside diameter toward the distal end. The portion of the first wire 2 possessing the progressively smaller outside diameter is referred to as the progressively-smaller-outside-diameter portion 15. By virtue of the progressively-smaller-outside-diameter portion 15, the rigidity (bending rigidity and flexural rigidity) of the first wire 2 is progressively smaller toward the distal end. As a result, the distal end portion of the guide wire 1 is pliable for an increased ability to follow blood vessels and higher safety, and is inhibited or prevented from being kinked.

In the illustrated embodiment, the progressively-smaller-outside-diameter portion 15 is provided as a portion of the first wire 2. However, the progressively-smaller-outside-diameter portion 15 may be provided along the entire length of the first wire 2 so that the first wire decreases in outer diameter from the proximal end to the distal end. The progressively-smaller-outside-diameter portion 15 has a taper angle (the ratio at which the outside diameter decreases) which may be constant along the longitudinal direction of the first wire 2 or which may vary along the longitudinal direction of the first wire 2. For example, the progressively-smaller-outside-diameter portion 15 may have a plurality of alternately repeating regions where the taper angle (the rate at which the outside diameter decreases) is relatively large and relatively small.

Also, the first wire 2 may include a portion whose outside diameter is constant along the longitudinal direction somewhere in the progressively-smaller-outside-diameter portion 15 or on the distal end of the progressively-smaller-outside-diameter portion 15. For example, the first wire 2 may include tapered portions in which the outside diameter is progressively reduced in the distal direction at respective locations along the longitudinal extent of the first wire 2, and other constant diameter portions in which the outside diameter is constant along the longitudinal extent and which are disposed between the tapered portions. The first wire 2 thus constructed offers advantages similar to those described above.

Moreover, the proximal end of the progressively-smaller-outside-diameter portion 15 may be positioned somewhere in the second wire 3. That is, the progressively-smaller-outside-diameter portion 15 may extend across the boundary (brazed region 14) between the first wire 2 and the second wire 3.

In the present embodiment, the first wire 2 is made of an alloy containing Ti and a transition metal other than Ti and Cr.

The transition metal other than Ti and Cr may be Fe, Co, Ni, V, Mn, Nb, Mo, Ag, Ta, W, or the like, and may be one of these metals or a combination of two or more of these metals.

The material of the first wire 2 should preferably be a pseudoelastic alloy (including superelastic alloy) among alloys containing Ti and the above transition metals. More preferably, the material of the first wire 2 should be a superelastic alloy. The superelastic alloy is relatively pliable, has recoverability, and is less liable to remain bent when it is bent. If the first wire 2 is made of a superelastic alloy, the distal end portion of the guide wire 1 is sufficiently flexible and recoverable when it is bent, has an increased ability to follow blood vessels that are curved and bent intricately, and is of excellent operability. Furthermore, as the first wire 2 is less liable to remain bent due to its recoverability even when the first wire 2 is repeatedly curved and flexurally deformed, the first wire 2 is prevented from having its operability lowered due to the tendency to remain bent which would otherwise be developed during use of the guide wire 1.

The superelastic alloy includes those which exhibit different tensile stress vs. strain curves (i.e., the superelastic alloys which can be used here are not limited to superelastic alloys having a particular tensile stress vs. strain curve), those which have transformation points such As (austenite start temperature), Af (austenite finish temperature), Ms (martensite start temperature), Mf (martensite finish temperature), etc. measurable clearly or not, and those which are largely deformed (strained) under stresses and return to their original shape upon removal of the stresses.

Preferable compositions of the superelastic alloy include an Ni—Ti-based alloy such as an Ni—Ti alloy containing 49 to 52 atomic % of Ni, etc. The superelastic alloy, which is typified by the Ni—Ti-based alloy, is excellent in its ability to adhere closely to a covering layer 5 to be described later.

The distal end of the second wire 3 is joined (connected) to the proximal end of the first wire 2 by brazing. The second wire 3 may be made of a wire material, and should preferably be made of an elastic wire material The length of the second wire 3 is not limited to any particular value, but should preferably be in the range from about 20 to 4800 mm.

The second wire 3 should preferably be made of a material having a greater modulus of elasticity (Young's modulus (tensile modulus), modulus of rigidity (shear modulus), bulk modulus) than the material of the first wire 2. The second wire 3 is thus of appropriate rigidity (bending rigidity and flexural rigidity), making the guide wire 1 sufficiently rigid to improve its pushability (ability to be pushed in) and its torque transmittability for excellent operability upon insertion of the guide wire 1.

According to the present embodiment, the second wire 3 is made of an alloy containing Cr and a transition metal other than Cr and Ti. The transition metal other than Cr and Ti may be any of the metals described above as the transition metal other than Ti and Cr.

The material of the second wire 3 should preferably be, among the alloys containing Cr and the above transition metals, stainless steel such as type 304, 303, 316, 316L, 316J1, 316J1L, 405, 430, 434, 444, 429, 430F, 302, or the like, or a cobalt-based alloy such as a Co—Ni—Cr-based alloy.

Of these materials, the cobalt-based alloy is preferable as it possesses, in the form of a wire, a relatively high modulus of elasticity and an appropriate elastic limit. Therefore, the second wire 3 made of a cobalt-based alloy has an excellent torque transmitting capability and is less susceptible to problems such as buckling. The second wire 3 made of an alloy such as a Co—Ni—Cr-based alloy is well able to exhibit the above advantages. The alloy of the above composition is flexible when deformed at normal temperature. Therefore, the wire can be easily deformed to a desired shape when it is in use. The alloy of the above composition also has a high modulus of elasticity, can be cold-formed even if it has a relatively high elastic limit, and can be reduced in diameter while sufficiently inhibiting or preventing itself from buckling because of the high elastic limitation. The wire of the alloy is flexible and rigid enough to be inserted into a given region.

The Co—Ni—Cr-based alloy should preferably be an alloy including 28 to 50 wt % of Co, 10 to 30 wt % of Ni, 10 to 30 wt % of Cr, and the remainder Fe, or an alloy similar to the above alloy, except that one or more of the elements Co, Ni and Cr may be partly replaced with another element (substitution element). The inclusion of the substitution element provides a particular advantage depending on its type. For example, if at least one element selected from Ti, Nb, Ta, Be, and Mo is included as the substitution element, the strength of the second wire 3 is further increased. If the Co—Ni—Cr-based alloy contains elements other than Co, Ni, Cr, the amount of those elements (all substitution elements) should preferably be 30 wt % or less.

Part of Co and Ni may be replaced with another element. For example, part of Ni may be replaced with Mn for improved machinability. Of the Co—Ni—Cr-based alloys, a Cr—Ni—Cr—Mo-based alloy is particularly preferable.

Specific compositions of the Co—Ni—Cr-based alloy include, for example: (1) 40 wt % of Co, 22 wt % of Ni, 25 wt % of Cr, 2 wt % of Mn, 0.17 wt % of C, 0.03 wt % of Be, and the remainder Fe; (2) 40 wt % of Co, 15 wt % of Ni, 20 wt % of Cr, 2 wt % of Mn, 7 wt % of Mo, 0.15 wt % of C, 0.03 wt % of Be, and the remainder Fe; (3) 42 wt % of Co, 13 wt % of Ni, 20 wt % of Cr, 1.6 wt % of Mn, 2 wt % of Mo, 2.8 wt % of W, 0.2 wt % of C, 0.04 wt % of Be, and the remainder Fe; (4) 45 wt % of Co, 21 wt % of Ni, 18 wt % of Cr, 1 wt % of Mn, 4 wt % of Mo, 1 wt % of Ti, 0.02 wt % of C, 0.3 wt % of Be, and the remainder Fe; (5) 34 wt % of Co, 21 wt % of Ni, 14 wt % of Cr, 0.5 wt % of Mn, 6 wt % of Mo, 2.5 wt % Nb, 0.5 wt % of Ta, and the remainder Fe, or the like. The Co—Ni—Cr-based alloy according to the disclosed embodiment includes these alloys.

If the second wire 3 is made of stainless steel, the guide wire 1 has an improved ability to be pushed in and an improved torque transmittability.

With respect to a specific combination of the first wire 2 and the second wire 3, it is preferable that the first wire 2 be made of a superelastic alloy containing Ti and the second wire 3 be made of a Co—Ni—Cr-based alloy or stainless steel. This specific combination makes the ability to be pushed in and the torque transmittability further improved.

With the illustrated structure, the second wire 3 is of a substantially constant outside diameter throughout its entire length. However, the second wire 3 may include a portion whose outside diameter varies in the longitudinal direction.

The superelastic alloy of the first wire 2 should preferably be an Ni—Ti-based alloy from the standpoint of the pliability and recoverability of the distal end portion thereof.

In the present embodiment, the first wire 2 and the second wire 3 are joined together to form the wire body 10. However, the wire body 10 may include three or more wire materials joined together.

The coil 4 includes a member formed by helically winding a blank wire (thin wire), and is disposed in covering relation to the distal end portion of the first wire 2. With the illustrated structure, the distal end portion of the first wire 2 is inserted substantially centrally in the coil 4 out of contact with the inner surface of the coil 4. The brazed region 14, to be described later, is proximally positioned relative to the proximal end of the coil 4.

With the illustrated structure, adjacent turns of the helically coiled blank wire of the coil 4 are spaced from each other by small gaps therebetween when no external forces are applied to the coil 4. However, the coil 4 can be configured so that adjacent turns of the helically coiled blank wire are in contact with each other with no gaps therebetween when no external forces are applied to the coil 4.

The coil 4 should be made of a metal material. According to the present embodiment, the metal material of the coil 4 may be stainless steel, a superelastic alloy, a cobalt-based alloy, a precious metal such as gold, platinum, tungsten, or the like, or an alloy containing any of these materials. If the coil 4 is made of an X-ray-impermeable material such as a precious metal, the guide wire 1 is compatible with X-ray angiography, so that the guide wire 1 can be inserted into a living body while the tip end portion thereof is being positionally confirmed under X-ray angiography.

The coil 4 may have its distal and proximal end portions made of different materials. For example, the distal end portion of the coil 4 may include a coil made of an X-ray-impermeable material and the proximal end portion thereof may include a coil made of a relatively X-ray-permeable material such as stainless steel or the like. The total length of the coil 4 is not limited to any values, but should preferably be in the range from about 5 to 500 mm.

According to the disclosed and illustrated embodiment, the coil 4 has its proximal and distal ends fixed to the first wire 2 by respective fastening materials 11, 12. The coil 4 also has an intermediate portion (closer to the distal end) fixed to the first wire 2 by a fastening material 13. The fastening materials 11, 12, 13 include a solder (brazing material) or an adhesive. The coil 4 may be fixed to the first wire 2 by welding, for example, rather than the fastening materials. The fixing material 12 should have a round distal end surface for protecting the inner blood vessel wall against damage.

The coil 4 thus placed on the first wire 2 reduces the area of contact of the first wire 2, resulting in reduced sliding resistance. As a result, the operability of the guide wire 1 is increased.

The blank wire of the coil 4 is preferably circular in cross-sectional shape. However, the cross-sectional shape of the blank wire is not limited in this regard as it may be a blank wire possessing, for example, an elliptical cross-sectional shape or a quadrangular (particularly, rectangular) cross-sectional shape.

The first wire 2 and the second wire 3 are joined (fixed) to each other by brazing at the brazed region function) 14. The brazed region 14 has a high bonding strength and allows the torsional torque and the pushing force to be transmitted reliably from the second wire 3 to the first wire 2.

In the brazed region 14, the brazing material that is interposed between the first wire 2 and the second wire 3 firmly joins the first wire 2 and the second wire 3 to each other based on the diffusion and anchoring effect in the first wire 2 and the second wire 3. Specifically, the proximal end face 21 of the first wire 2 to be joined to the second wire 3 and the distal end face 31 of the second wire 3 to be joined to the first wire 2 are joined to the brazing material, thereby joining the first wire 2 and the second wire 3 to each other.

As described above, the first wire 2 is made of an alloy containing Ti and a transition metal other than Ti and Cr, and the second wire 3 is made of an alloy containing Cr and a transition metal other than Cr and Ti.

Ti and Cr react with oxygen in the atmosphere to form oxides such as $TiO_2$ and $Cr_2O_3$, respectively, producing highly chemically stable films. Since the first wire 2 and the second wire 3 are oxidized from their surfaces exposed to the atmosphere, their surfaces are covered with the oxide films.

Heretofore, there has been proposed a guide wire including wires, which have oxide films formed thereon, brazed to each other. However, due to chemically stable properties of the oxide films, the brazing material fails to sufficiently wet the oxide films. The oxide films serve as protective layers which prevent the brazing material from acting directly on the base materials (alloys) of the first and second wires 2, 3. Therefore, it has not been possible previously to firmly braze the first and second wires 2, 3 to each other.

The oxide films also prevent the first and second wires 2, 3 from being joined to each other when they are welded to each other. It has thus been difficult to firmly weld the first and second wires 2, 3 to each other.

According to the present invention, a brazing material containing a metal whose ionization tendency is more basic than Ti and Cr is used to braze the first and second wires 2, 3 to each other.

The metal whose ionization tendency is more basic than Ti and Cr refers to a metal whose ionization tendency is greater than Ti and Cr and which is more ionizable than Ti and Cr.

If the brazing material contains a metal whose ionization tendency is more basic than Ti and Cr, the metal acts on the oxide films, deprives the oxide films of $TiO_2$ and $Cr_2O_3$ of oxygen molecules, and reduce these oxides. The oxide films are thus modified (removed) to allow the brazing material to act directly on the base materials of the first and second wires 2, 3. As a result, the first and second wires 2, 3 are firmly joined to each other based on the diffusion and anchoring effect. Though the first and second wires 2, 3 have relatively small joining areas, they are firmly joined to each other to produce the guide wire 1 which is highly reliable.

Metals whose ionization tendency is more basic than Ti and Cr include, for example, Li, Cs, Rb, K, Ba, Sr, Ca, Na, La, Mg, etc. Though one of these metals may be used alone or two or more of them may be used in combination, Mg is particularly preferable because Mg is available relatively inexpensively. Another advantage of Mg is that when Mg reacts with another metal, it hardly produces a hard brittle ionically-bonded substance. Accordingly, Mg is able to join the first and second wires 2, 3 firmly to each other, and the formed brazed region 14 is of relatively excellent toughness. Mg is thus suitable for use as a constituent of the brazing material. In other words, Mg used as a constituent of the brazing material functions as a reducing agent for the oxide films of $TiO_2$ and $Cr_2O_3$.

The content of Mg in the brazing material should preferably be in the range from 10 to 96 atm % and more preferably in the range from 15 to 92 atm %. Mg thus contained in the brazing material sufficiently acts on the oxide films to reliably remove the oxide films.

If the content of Mg exceeds the upper limit of the above range, the properties of Mg become dominant in the brazing material. Since Mg is relatively hard and brittle, Mg contained in excess of the upper limit of the above range tends to reduce mechanical properties of the brazing material, e.g., toughness and ductility.

The brazing material should preferably include a eutectic alloy having an eutectic composition. A brazing material including a eutectic alloy has its melting point lowered by selecting a composition near the eutectic point. Depending on the melting point, the brazing material allows the first and second wires 2, 3 to be brazed easily without the need for an expensive heating device of excellent heat resistance.

A brazing material including a eutectic alloy is also highly flowable when melted by selecting a composition near the eutectic point. The brazing material can flow uniformly and reliably to the end face 21 of the first wire 2 and the end face 31 of the second wire 3 when the first and second wires 2, 3 are brazed by the brazing material. In particular, if the end faces 21, 31 have rough surfaces, the brazing material including a eutectic alloy can flow to fill up recesses in the rough surfaces. Therefore, the surfaces into which the brazing material is diffused have a wide area and provide a relatively outstanding anchoring effect, resulting in an increased bonding strength.

The brazing material including an eutectic alloy resides in that a temperature range in which a solid phase and a liquid phase exist together (solid-liquid coexistent range) is short (narrow) in the vicinity of the eutectic point. In other words, the solid phase and the liquid phase of the brazing material are adjacent to each other in terms of temperature.

If a brazing material including a eutectic alloy is gradually cooled from a liquid phase (molten state), the brazing material abruptly solidifies when the temperature drops even slightly from the lowest temperature at which the brazing material is in the liquid phase. The brazing material is thus inhibited or prevented from becoming irregular in composition and crystallizes into a solid structure having a relatively uniform composition.

On the other hand, a brazing material including a nonuetectic alloy which does not have an eutectic composition has a long (wide) solid-liquid coexistent range. If such a brazing material is gradually cooled from a liquid phase, the brazing material tends to be held in a state wherein the solid phase and the liquid phase exist together for a relatively long time. Consequently, a solid structure having a relatively high melting point, e.g., an intermetallic compound or the like, selectively crystallizes, with the result that the brazing material tends to become irregular in its solid phase after it has solidified. The irregular solid brazing material is liable to have degraded mechanical properties (toughness, etc.) and chemical properties (weather-resistance, chemical resistance, etc.).

In view of the above considerations, a brazing material including a eutectic alloy has excellent mechanical properties and chemical properties by selecting a composition in the vicinity of the eutectic point.

When a brazing material solidifies, its volume generally decreases. Such a volumetric reduction is referred to as solidification shrinkage. A brazing material that includes an eutectic alloy undergoes generally uniform solidification shrinkage in its entirety by selecting a composition in the vicinity of the eutectic point. Therefore, the brazing material does not develop interstices and voids therein while it is solidifying to braze the first and second wires 2, 3 to each other.

Furthermore, a brazing material including an eutectic alloy solidifies at different times depending on the composition. Upon solidification shrinkage, interstices (spaces) are liable to be produced between a portion which is slow in crystallization and a portion which is fast in crystallization. Such interstices tend to degrade the properties of the brazing material and to lower the reliability of the brazed joint because they remain in the brazing material after it has solidified.

In view of the above considerations, a brazing material including a eutectic alloy includes no voids and can braze the first and second wires 2, 3 to each other highly reliably by selecting a composition in the vicinity of the eutectic point.

The brazing material used according to the present invention should preferably include an alloy of Mg and Ag, Ni, Au or Cu. Since Ag, Ni, Au, and Cu are of excellent mechanical properties, the brazing material which includes an alloy of one of these metals and Mg is effective to reliably remove the oxide films and has excellent mechanical properties. Therefore, when the first and second wires 2, 3 are brazed to each other by the brazing material, the guide wire 1 has the brazed region 14 which is of excellent mechanical properties.

The brazing material may include, for example, an Ag—Mg alloy, an Ni—Mg alloy, an Au—Mg alloy or a Cu—Mg alloy. Since each of the Ag—Mg alloy, the Ni—Mg alloy, the Au—Mg alloy, and the Cu—Mg alloy is an eutectic alloy, they provide the advantages such as described above.

Using the brazing material including the above eutectic alloy, the guide wire 1 is produced which includes the first and second wires 2, 3 firmly brazed to each other.

Figure 3:
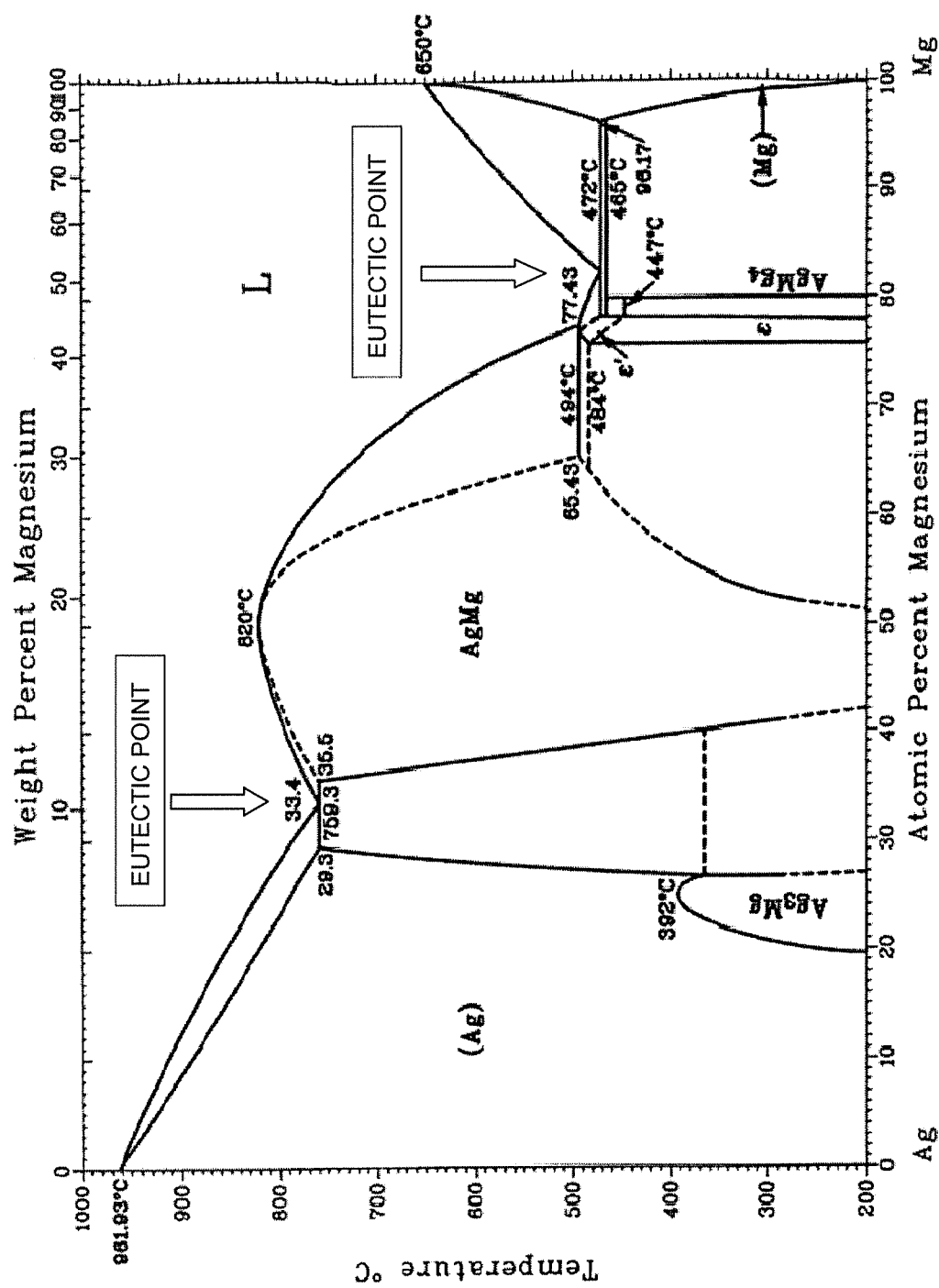
FIG. 3 is a phase diagram of an Ag—Mg alloy.

In view of the above considerations, the brazing material including the above eutectic alloy should preferably have a composition near the eutectic point. Specifically, for example, an Ag—Mg alloy has a eutectic composition of 66.6 atm % of Ag and 33.4 atm % of Mg or 17.6 atm % of Ag and 82.4 atm % of Mg, as indicated by the phase diagram shown in FIG. 3.

Based on the above specific numerical values, the content of Mg in a brazing material which includes an Ag—Mg alloy should preferably be in the range from 30 to 36 atm % and more preferably in the range from 32 to 34 atm %. Alternatively, the content of Mg in a brazing material which includes an Ag—Mg alloy should preferably be in the range from 79 to 85 atm % and more preferably in the range from 81 to 83 atm %.

If the content of Mg is kept in the above ranges, the brazing material is capable of sufficiently removing the oxide films with Mg and is highly flowable when melted. Accordingly, the guide wire 1 which is brazed using the brazing material possesses excellent mechanical properties and is highly reliable.

Figure 4:
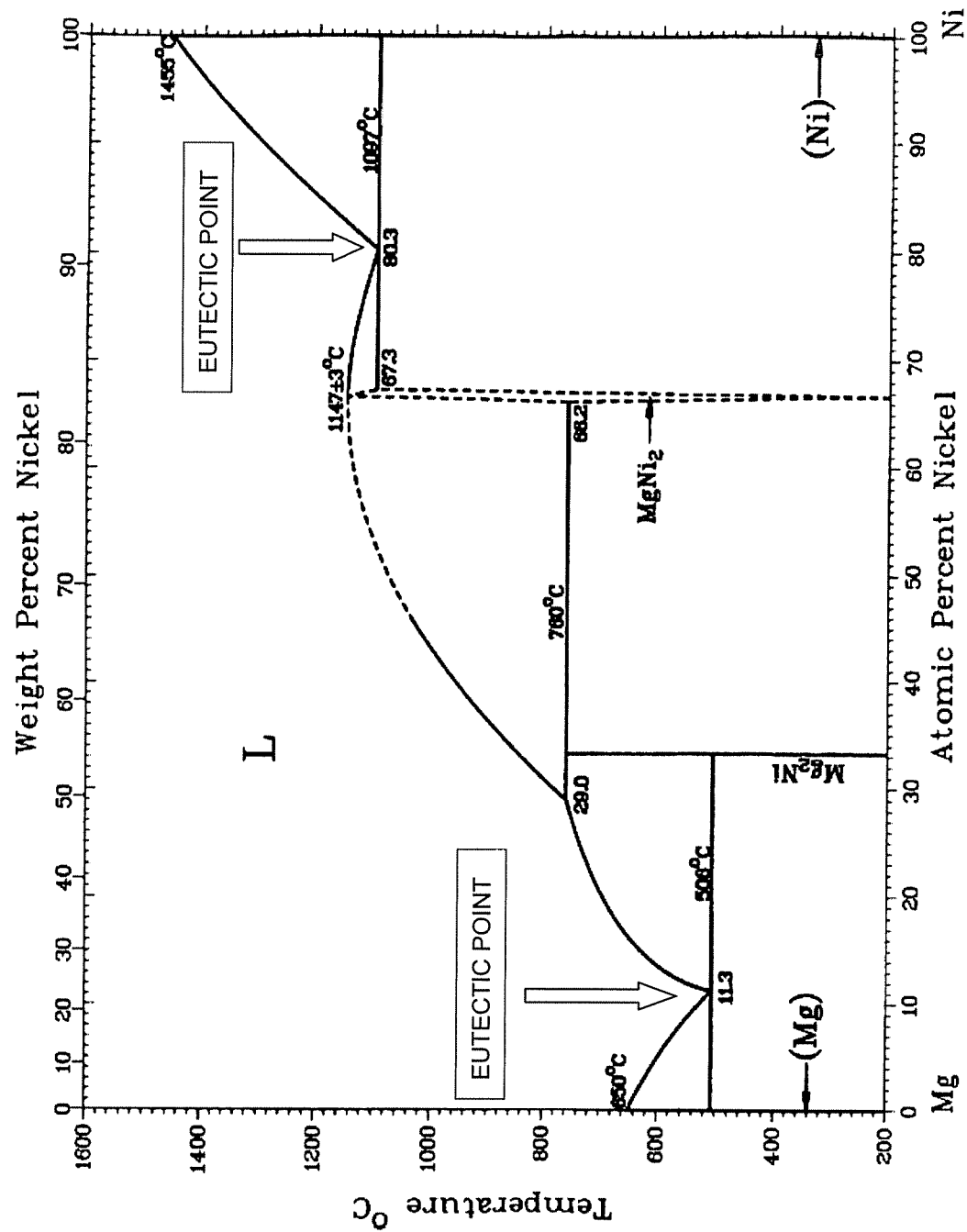
FIG. 4 is a phase diagram of an Ni—Mg alloy.

An Ni—Mg alloy has a eutectic composition of 80.3 atm % of Ni and 19.7 atm % of Mg or 11.3 atm % of Ni and 88.7 atm % of Mg, as indicated by a phase diagram shown in FIG. 4.

Based on the above specific numerical values, the content of Mg in a brazing material which includes an Ni—Mg alloy should preferably be in the range from 17 to 23 atm % and more preferably in the range from 19 to 21 atm %. Alternatively, the content of Mg in a brazing material which includes an Ni—Mg alloy should preferably be in the range from 86 to 92 atm % and more preferably in the range from 88 to 90 atm %.

If the content of Mg is kept in the above ranges, the brazing material is capable of sufficiently removing the oxide films with Mg and is highly flowable when melted. Accordingly, the guide wire 1 which is brazed using the brazing material possesses excellent mechanical properties and is highly reliable.

The content of Mg in an Au—Mg alloy should preferably be in the range from 30 to 96 atm %.

If the content of Mg is kept in the above range, then the brazing material of the Au—Mg alloy is of excellent mechanical properties and has an excellent ability to remove the oxide films.

The brazing material of the Au—Mg alloy should have a composition near the eutectic point. Specifically, for example, an Au—Mg alloy has a eutectic composition of 67.5 atm % of Au and 32.5 atm % of Mg, or 36.0 atm % of Au and 64.0 atm % of Mg, or 30.8 atm % of Au and 69.2 atm % of Mg, or 7.0 atm % of Au and 93.0 atm % of Mg, as indicated by a phase diagram shown in FIG. 5(*a*).

Based on the above specific numerical values, the content of Mg in a brazing material which includes an Au—Mg alloy should preferably be in the range from 30 to 36 atm % and more preferably in the range from 32 to 34 atm %. Alternatively, the content of Mg in a brazing material which includes an Au—Mg alloy should preferably be in the range from 61 to 72 atm % and more preferably in the range from 63 to 65 atm % or from 68 to 70 atm %. Further alternatively, the content of Mg in a brazing material which includes an Au—Mg alloy should preferably be in the range from 90 to 96 atm % and more preferably in the range from 92 to 94 atm %.

If the content of Mg is kept in the above ranges, the brazing material is capable of sufficiently removing the oxide films with Mg and is highly flowable when melted. Accordingly, the guide wire 1 which is brazed using the brazing material possesses excellent mechanical properties and is highly reliable.

Since the brazing material of the Au—Mg alloy contains a precious metal of Au, it is of excellent weather-resistance and chemical resistance. Therefore, the guide wire 1 which is brazed using the brazing material is highly reliable.

The content of Mg in a Cu—Mg alloy should preferably be in the range from 10 to 88 atm % and more preferably in the range from 20 to 88 atm %.

If the content of Mg is kept in the above range, the brazing material of the Cu—Mg alloy possesses excellent mechanical properties and has an excellent ability to remove the oxide films.

The brazing material of the Cu—Mg alloy should have a composition near the eutectic point. Specifically, for example, a Cu—Mg alloy has a eutectic composition of 76.9 atm % of Cu and 23.1 atm % of Mg, or 42.0 atm % of Cu and 58.0 atm % of Mg, or 14.5 atm % of Cu and 85.5 atm % of Mg, as indicated by a phase diagram shown in FIG. 5($b$).

Based on the above specific numerical values, the content of Mg in a brazing material which includes a Cu—Mg alloy should preferably be in the range from 20 to 26 atm % and more preferably in the range from 22 to 24 atm %. Alternatively, the content of Mg in a brazing material which includes a Cu—Mg alloy should preferably be in the range from 55 to 61 atm % and more preferably in the range from 57 to 59 atm %. Further alternatively, the content of Mg in a brazing material which includes a Cu—Mg alloy should preferably be in the range from 82 to 88 atm % and more preferably in the range from 84 to 86 atm %.

If the content of Mg is kept in the above ranges, the brazing material is capable of sufficiently removing the oxide films with Mg and is highly flowable when melted. Accordingly, the guide wire 1 which is brazed using the brazing material possesses excellent mechanical properties and is highly reliable.

According to the disclosed embodiment here, the proximal end face 21 of the first wire 2 to be joined to the second wire 3 and the distal end face 31 of the second wire 3 to be joined to the first wire 2 include flat surfaces, respectively, which are perpendicular to the axial direction (longitudinal direction) of the wires. Therefore, the machining process for forming the end faces 21, 31 to be joined is relatively simple, and the above advantages can be achieved without significantly increasing the complexity of the process of manufacturing the guide wire 1.

It is to be understood, however, that the end faces 21, 31 to be joined may be inclined to a plane perpendicular to the axial direction (longitudinal direction) of the wires, or may include concave or convex surfaces. These inclined, concave, or convex surfaces give a wider area to the surfaces (the end faces to be joined) which contribute to the brazing, allowing the first and second wires 2, 3 to be firmly brazed to each other.

While the end faces 21, 31 to be joined may be flat surfaces, respectively, they should preferably be rough surfaces. The brazing material finds itself into the recesses in the rough surfaces to provide a strong anchoring effect between the brazing material and the end faces 21, 31 to be joined. As a consequence, the first and second wires 2, 3 can be firmly joined to each other by the brazing material.

The first and second wires 2, 3 may be brazed to each other by various processes not specifically limited to any particular method. For example, suitable processes include a torch brazing process for melting a brazing material with a gas flame ejected from a torch to braze workpieces, an arc brazing process for melting a brazing material with an arc generated between electrodes to braze workpieces, and an in-furnace brazing process for melting a brazing material in a furnace with a predetermined atmosphere developed therein to braze workpieces.

Procedures (steps) (1) through (4) for brazing the first and second wires 2, 3 to each other will be described below with reference to FIG. 6.

In a first procedure (1), the first and second wires 2, 3, fixed in place by fixing jigs (not shown) are provided.

In a subsequent second procedure (2), a brazing material 140 is disposed between the first and second wires 2, 3. The brazing material 140 may be given in various forms not limited to any particular shapes, e.g., a plate form, a linear form, a granular (powdery) form, a paste form, etc.

In a subsequent third procedure (3), the brazing material 140 is melted under heat. The melted brazing material 140 fills up the gap between the end face 21 of the first wire 2 and the end face 31 of the second wire 3. Thereafter, the brazing material 140 solidifies as it is naturally or forcibly cooled. As a result, the first and second wires 2, 3 are firmly brazed to each other by the brazing material 140 based on the diffusion and anchoring effect thereof.

Figure 2:
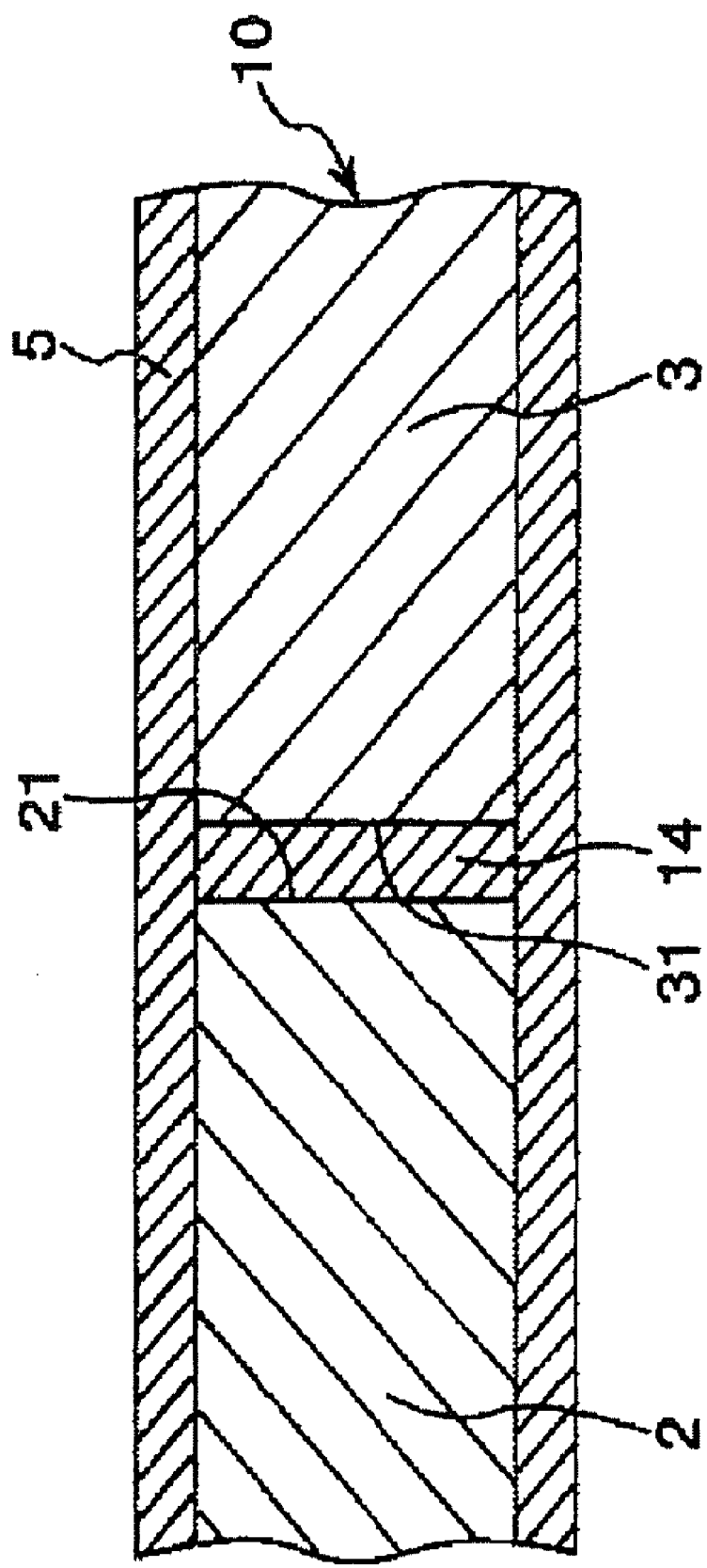
FIG. 2 is an enlarged fragmentary cross-sectional view of a brazed region of the guide wire shown in FIG. 1.

The thickness of the brazed region 14 thus formed (i.e., the spaced distance between the end faces 21, 31 shown in FIG. 2) should preferably be in the range from 5 to 500 μm and more preferably from 10 to 300 μm, for better mechanical properties of the brazed region 14.

In the second procedure (2), the amount of brazing material to be disposed between the first and second wires 2, 3 should preferably be adjusted so that the thickness of the brazed region 14 achieves the spaced distance mentioned above.

If necessary, any protrusions on the outer circumferential surface of the area that has been brazed (the brazed region 14) should be removed to make the outer circumferential surface of the brazed region 14 substantially smooth. The protrusions may be removed by a mechanical process such as grinding or polishing, or a chemical process such as etching or the like.

Then, in a subsequent fourth procedure (4), the portion of the first wire 2 which is positioned closer to the distal end than the connected area (the brazed region 14) is ground or polished into the progressively-smaller-outside-diameter portion 15 whose outside diameter is progressively smaller toward the distal end.

The outer circumferential surface (outer surface) of the wire body 10 is covered entirely or partially with a covering layer 5. The covering layer 5 may be formed for various purposes. For example, the covering layer 5 can serve to reduce the friction (frictional resistance) of the guide wire 1 for increased slidability, thereby increasing the operability of the guide wire 1.

In order to serve the above purpose, the covering layer 5 should preferably be made of a material capable of reducing friction. The frictional resistance (sliding resistance) between the guide wire 1 and the inner wall of the catheter that is used with the guide wire 1 is reduced to increase slidability, allowing the guide wire 1 to be better operated in the catheter.

Moreover, since the sliding resistance to the guide wire 1 is reduced, when the guide wire 1 is moved and/or turned in the catheter, the guide wire 1 is relatively reliably prevented from being kinked (bent) or twisted, particularly in the vicinity of the brazed region.

The material capable of reducing friction may be polyolefin such as polyethylene, polypropylene, or the like, polyvinyl chloride, polyester (PET, PBT, or the like), polyamide, polyimide, polyurethane, polystyrene, polycarbonate, silicone resin, fluororesin (PTFE, ETFE, or the like), or a composite material thereof.

If, among these materials, fluororesin (or a composite material containing fluororesin) is used, it is effective to reduce the frictional resistance (sliding resistance) between the guide wire 1 and the inner wall of the catheter for increased slidability. The guide wire 1 is thus allowed to be better operated in the catheter. Moreover, when the guide wire 1 is moved and/or turned in the catheter, the guide wire 1 is reliably prevented from being kinked (bent) or twisted particularly in the vicinity of the brazed region. If fluororesin (or a composite material containing fluororesin) is used, it is customary to apply the resin material as it is heated to the wire body 10 by baking, spraying, or the like. The wire body 10 and the covering layer 5 are thus held in excellent close adhesion to each other.

If the covering layer 5 is made of silicone resin (or a composite material containing silicone resin), when the covering layer 5 is formed (to cover the wire body 10), the covering layer 5 is reliably and firmly held in close adhesion to the wire body 10. Specifically, if the covering layer 5 is made of silicone resin (or a composite material containing silicone resin), since it may be a reaction-curable material, the covering layer 5 may be formed at room temperature. If the covering layer 5 is formed at room temperature, the wire body 10 can be relatively easily coated, and the guide wire can be operated with the sufficient bonding strength at the brazed region 14 between the first and second wires 2, 3.

Another preferable example of the material which is capable of reducing friction is a hydrophilic material or a hydrophobic material. Particularly, a hydrophilic material is preferable.

The hydrophilic material may be cellulose-based polymeric material, polyethylene-oxide-based polymeric material, maleic-anhydride-based polymeric material (e.g., maleic anhydride copolymer such as methylvinylether-maleic anhydride copolymer), acrylamide-based polymeric material (e.g., polyacrylamide or polyglycidylmethacrylate-dimethylacrylamide (PGMA-DMMA) block copolymer), water-soluble nylon, polyvinyl alcohol, polyvinyl pyrrolidone, or the like.

When the hydrophilic material is wetted (absorbs water), it provides lubrication to reduce friction (sliding resistance) between the guide wire 1 and the inner wall of the catheter that is used with the guide wire 1. The slidability of the guide wire 1 is increased to improve the operability of the guide wire 1 in the catheter.

The covering layer 5 may be formed on the entire length of the wire body 10 or a longitudinal portion of the wire body 10. However, the covering layer 5 should preferably be formed at least in covering relation to the brazed region 14, i.e., on a portion including the brazed region 14. Even if the outer circumferential surface of the brazed region 14 has steps, burrs, or the like, since they are covered with the covering layer 5, the slidability of the guide wire 1 is maintained. The slidability is further increased because the covering layer 5 has a substantially uniform outside diameter.

Though the thickness of the covering layer 5 is not limited to any values, the thickness (average) should preferably be in the range from 1 to 20 μm and more particularly from 2 to 10 μm. If the covering layer 5 is too thin, the purpose for which the covering layer 5 is formed is not sufficiently served, and the covering layer 5 may possibly peel off. If the covering layer 5 is too thick, the properties of the wire may be impaired, and the covering layer 5 may possibly peel off.

According to this disclosed embodiment, the outer circumferential surface (outer surface) of the wire body 10 may be treated (chemically or thermally) to increase the close adhesion to the covering layer 5, or an intermediate layer may be disposed on the outer circumferential surface (outer surface) of the wire body 10 to increase the close adhesion to the covering layer 5.

A guide wire constituting an interventional medical device according to a second embodiment is described below with reference to FIG. 7. Those parts of the second embodiment which are identical to the first embodiment are identified by common reference numerals and a detailed description of such common features is not repeated. The description below primarily describes differences between the second embodiment relative to the first embodiment described above.

According to this embodiment, the first wire 2 and the coil 4 are described as examples of the first member and the second member. Specifically, the guide wire 1 according to the present embodiment has the first wire 2 and the coil 4 brazed to each other by the brazing material disclosed herein.

In the guide wire 1 according to this embodiment, the first wire 2 is made of an alloy containing Ti and a transition metal other than Ti and Cr, as with the first embodiment. Also, according to the present embodiment, the coil 4 is made of an alloy containing Cr and a transition metal other than Cr and Ti.

The coil 4 is fixed to the first wire 2 at brazed regions 16, 17, 18. Each of the brazed regions 16, 17, 18 is brazed using the brazing material described above. The brazed regions 16, 17, 18 allow the first wire 2 and the coil 4 to be firmly brazed to each other. As a result, the guide wire 1 which is highly reliable is obtained.

According to the present embodiment, specific examples of the material of the coil 4 include, for example, stainless steel such as type 304, 303, 316, 316L, 316J1, 316J1L, 405, 430, 434, 444, 429, 430F, 302, or the like, or a Cr-containing alloy such as an Co—Ni—Cr-based alloy.

In the present embodiment, the first wire 2 and the coil 4 are fixed to each other at the three brazed regions 16, 17, 18. At one or two of the three regions, the first wire 2 and the coil 4 may be fixed to each other by any methods, e.g., adhesive bonding, welding, or the like.

In the guide wire 1 according to the present embodiment, the first wire 2 and the second wire 3 may be connected (fixed) to each other by any methods, e.g., brazing, welding, or the like.

In the present embodiment, the wire body 10 is constructed by connecting the first and second wires 2, 3 to each other. However, the wire body 10 may be constructed of a single continuous material or may be constructed of three or more blank wires that are connected together.

If the wire body 10 is constructed of a single material, the wire body 10 should preferably be made of an Ni—Ti-based alloy.

A guide wire constituting an interventional medical device according to a third embodiment is described below with reference to FIG. 8(*a*). Features of the third embodiment which are identical to the first embodiment are identified by common reference numerals and a detailed description of such common features is not repeated. The description below primarily describes differences between the third embodiment relative to the first embodiment described above.

According to this third embodiment, the wire body 10 has a tubular body 6 extending over the proximal end portion of the first wire 2 and the distal end portion of the second wire 3 to cover the outer circumferential surface of the proximal end portion of the first wire 2 and the outer circumferential surface of the distal end portion of the second wire 3. The covering layer 5 is disposed on the outer circumferential surface (outer surface) of the wire body 10. That is, the covering layer 5 covers the outer circumferential surface of the tubular body 6, the outer circumferential surface of the portion of the first wire 2 that extends distally beyond the tubular portion 6 and the outer circumferential surface of the portion of the second wire 3 that extends proximally beyond the tubular portion 6.

According to the present embodiment, the tubular body 6 and the second wire 3 are described as examples of the first member and the second member respectively. Specifically, in the wire body 10 according to the present embodiment, the tubular body 6 (the first member) and the distal end portion of the second wire 3 (the second member) are brazed to each other by the brazing material described above. That is, a brazed region 62 shown in FIG. 8(a) is made of the brazing material.

According to this embodiment, the tubular body 6 is made of the same material as the first wire 2. In other words, the tubular body 6 is made of an alloy containing Ti and a transition metal other than Ti and Cr. Therefore, as with the first embodiment, the tubular body 6 which corresponds to the first member and the second wire 3 which corresponds to the second member can be firmly joined to each other by being brazed using the brazing material described in detail above.

Since the first wire 2 and the tubular body 6 are made of the same material, a joined region 61 therebetween may be joined by any methods. In other words, the joined region 61 may be joined relatively easily by welding, brazing, or the like without the need for the brazing material disclosed herein.

The portion of the proximal end portion of the first wire 2 which is covered with the tubular body 6 should preferably have an outside diameter smaller than the outside diameter of the adjoining portion of the first wire 2 (i.e., the portion of the first wire 2 distal of the distal end of the tubular body 6) as shown in FIG. 8(a). Similarly, the portion of the distal end portion of the second wire 3 which is covered with the tubular body 6 should preferably have an outside diameter smaller than the outside diameter of the adjoining portion of the second wire 3 (i.e., the portion of the second wire 3 proximal of the proximal end of the tubular body 6) as also shown in FIG. 8(a). With this arrangement, the outside diameter of the wire body 10 is less liable to have changes, increasing the slidability of the guide wire 1.

The difference between the outside diameters of the smaller-outside-diameter portion (hereinafter referred to as "reduced-diameter portion 22") of the first wire 2 and the portion greater in outside diameter than the reduced-diameter portion 22 (hereinafter referred to as "increased-diameter portion 23") of the first wire 2 should preferably be almost equal to the thickness (wall thickness) t of the tubular body 6 (see FIG. 8(a)). Similarly, the difference between the outside diameters of the smaller-outside-diameter portion (hereinafter referred to as "reduced-diameter portion 32") of the second wire 3 and the portion greater in outside diameter than the reduced-diameter portion 32 (hereinafter referred to as "increased-diameter portion 33") of the second wire 3 should preferably be almost equal to the thickness (wall thickness) t of the tubular body 6 (see FIG. 8(a)). Thus, any step in the outside diameter of the wire body 10 is further reduced.

A junction 24 between the reduced-diameter portion 22 and the increased-diameter portion 23, and a junction 34 between the reduced-diameter portion 32 and the increased-diameter portion 33, may be of a stepped shape, but should preferably be of a tapered shape as shown in FIG. 8(a).

A guide wire constituting an interventional medical device according to a fourth embodiment is described below with reference to FIG. 8(b). Features of the fourth embodiment which are identical to the first and third embodiment are identified by common reference numerals and a detailed description of such common features is not repeated. The description below primarily describes differences between the fourth embodiment relative to the first and third embodiments described above.

According to this fourth embodiment, the wire body 10 has a tubular body 6 extending over the proximal end portion of the first wire 2 and the distal end portion of the second wire 3 to cover the outer circumferential surface of the proximal end portion of the first wire 2 and the outer circumferential surface of the distal end portion of the second wire 3.

In this embodiment, the first wire 2 and the tubular body 6 constitute examples of the first member and the second member. Specifically, in the wire body 10 according to the present embodiment, the proximal end portion of the first wire 2 (the first member) and the tubular body 6 (the second member) are brazed to each other by the brazing material described previously. A brazed region 61 shown in FIG. 8(b) is made of the brazing material described previously.

According to this embodiment, the tubular body 6 is made of the same material as the second wire 3. In other words, the tubular body 6 is made of an alloy containing Cr and a transition metal other than Cr and Ti. Therefore, as with the first embodiment, the first wire 2 which corresponds to the first member and the tubular body 6 which corresponds to the second member can be firmly joined to each other by being brazed using the brazing material disclosed herein as described above.

In this embodiment, since the tubular body 6 and the second wire 3 are made of the same material, a joined region 62 therebetween may be joined or formed by any of a variety of methods. By way of example, the joined region 62 may be formed relatively easily by welding, brazing, or the like without the need for the brazing material as described herein.

The brazing material, the guide wires, and the joined assemblies described herein have been described above based on the illustrated embodiments. The present invention is not limited to the illustrated embodiments, as various parts or features of the guide wires may be replaced with other features or structure which perform the same or similar functions. Also, additional features and structures may be added. In addition, the disclosure here is applicable to medical devices, especially interventional medical devices, for example catheters, endoscopes, stent delivery devices, embolic coil deployment devices.

A guide wire may be constructed of a combination of a plurality of structures described in the above embodiments. Specifically, the first wire 2 and the second wire 3 may be brazed to each other by the brazing material disclosed herein, and the first wire 2 and the coil 4 may be brazed to each other by the brazing material described herein.

Alternatively, the first wire 2 and the second wire 3 may be brazed to each other by the brazing material disclosed here, and the tubular body 6 and the second wire 3 may be brazed to each other by the brazing material described herein.

Further alternatively, the first wire 2 and the second wire 3 may be brazed to each other by the disclosed brazing material, and the first wire 2 and the tubular body 6 may be brazed to each other by the disclosed brazing material.

In each of the above embodiments, the first wire and the second wire, and the first wire and the coil have been described by way of example as the first member and the second member which are brazed to each other by the disclosed brazing material. According to other examples of the first and second members, various shaped members such as eyeglass parts, dental braces, etc., for example, may be used as the first and second members, in addition to the tubular member joining the first and second members and at least one of the first and second members. When these members are brazed into a joined assembly, the joined assembly provides the same advantages as described above and is highly reliable.

The principles, embodiments and other aspects disclosed herein have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An interventional medical device comprising:
   a first member:
   a second member;
   the first and second members being brazed to each other by a brazing material;
   the brazing material comprising an eutectic alloy containing a metal whose ionization tendency is greater than both Ti and Cr;
   the metal comprising Mg; and
   the eutectic alloy having an eutectic composition.

2. The interventional medical device according to claim 1, wherein the first member is made of a Ni—Ti-based alloy and the second member is made of stainless steel.

3. The interventional medical device according to claim 1, wherein the interventional medical device is a guide wire comprising a wire body, the first member being a first wire and the second member being a second wire, a proximal end face of the first wire being brazed to a distal end face of the second wire by the brazing material.

4. The interventional medical device according to claim 1, wherein the interventional medical device is a guide wire comprising a wire body and a helical coil wound encircling at least a portion of the wire body, the wire body being the first member and the helical coil being the second member.

5. The interventional medical device according to claim 1, wherein the interventional medical device is a guide wire comprising a wire body, the wire body comprising a first wire possessing a proximal end and a second wire possessing a distal end, the distal end of the second wire facing the proximal end of the first wire, and a tubular member encircling the proximal end of the first wire and the distal end of the second wire, the first member being the first or second wire and the second member being the tubular member.

6. An interventional medical device comprising a first member and a second member, the first member being made of an alloy containing Ti (titanium) and a transition metal, the transition metal being other than Ti and other than Cr (chromium), the second member being made of an alloy containing Cr and a transition metal, the transition metal in the alloy of the second member being other than Cr and other than Ti, the first member and the second member being brazed to each other by a brazing material containing a metal whose ionization tendency is greater than both Ti and Cr, and
   wherein the brazing material is made of an eutectic alloy having an eutectic composition.

7. The interventional medical device according to claim 6, wherein the metal whose ionization tendency is more than Ti and Cr comprises Mg (magnesium).

8. The interventional medical device according to claim 6, wherein the brazing material is made of an alloy of Mg and additionally Ag (silver), Ni (nickel), Au (gold), or Cu (copper).

9. An interventional medical device comprising:
   a wire body comprised of a first wire and a second wire, the first and second wire each possessing opposite ends:
   one end of the second wire being brazed to the first wire by a brazing material;
   the wire body possessing a constant outer diameter portion at which the outer diameter of the wire body is constant;
   the constant outer diameter portion possessing an outer diameter in a range of about 0.2 mm to 1.2 mm;
   the brazing material comprising an eutectic alloy containing a metal whose ionization tendency is greater than the ionization tendency of both Ti and Cr;
   the metal comprising Mg; and
   a helical coil disposed on or around at least a portion of the first wire;
   the eutectic alloy having an eutectic composition.

10. The interventional medical device according to claim 9, wherein the brazing material is made of an alloy that includes Ag (silver), Ni (nickel), Au (gold), or Cu (copper).

11. The interventional medical device according to claim 9, further comprising a friction-reducing covering layer covering at least a portion of the first wire and at least a portion of the second wire.

12. The interventional medical device according to claim 9, wherein the first and second wires possess proximal and distal ends, the brazing material brazing together the proximal end of the first wire and the distal end of the second wire.

13. The interventional medical device according to claim 9, wherein said wire body comprises a catheter guide wire for insertion into a catheter.

14. The interventional medical device according to claim 13, wherein the first wire includes a progressively smaller outside diameter portion.

\* \* \* \* \*